(12) United States Patent
Pastore et al.

(10) Patent No.: US 12,138,319 B2
(45) Date of Patent: Nov. 12, 2024

(54) CHIMERIC PROTEIN AND RELATED GENIC TRANSFER TECHNOLOGY

(71) Applicants: Lucio Pastore, Naples (IT); Eleonora Leggiero, Naples (IT)

(72) Inventors: Lucio Pastore, Naples (IT); Eleonora Leggiero, Naples (IT)

(73) Assignees: Lucio Pastore, Naples (IT); Eleonora Leggiero, Naples (IT)

( * ) Notice: Subject to any disclaimer, the term of this patent is extended or adjusted under 35 U.S.C. 154(b) by 698 days.

(21) Appl. No.: 17/422,586

(22) PCT Filed: Jan. 15, 2020

(86) PCT No.: PCT/IT2020/000004
§ 371 (c)(1),
(2) Date: Jul. 13, 2021

(87) PCT Pub. No.: WO2020/148793
PCT Pub. Date: Jul. 23, 2020

(65) Prior Publication Data
US 2022/0313842 A1    Oct. 6, 2022

(30) Foreign Application Priority Data
Jan. 16, 2019    (IT) .......................... 102019000000651

(51) Int. Cl.
| | |
|---|---|
| *A61K 48/00* | (2006.01) |
| *A61K 9/00* | (2006.01) |
| *A61K 38/00* | (2006.01) |
| *C07K 14/005* | (2006.01) |
| *C07K 14/47* | (2006.01) |
| *C07K 14/705* | (2006.01) |
| *C12N 7/00* | (2006.01) |
| *C12N 15/62* | (2006.01) |
| *C12N 15/86* | (2006.01) |

(52) U.S. Cl.
CPC ........ *A61K 48/0066* (2013.01); *A61K 9/0019* (2013.01); *A61K 48/0058* (2013.01); *C07K 14/005* (2013.01); *C07K 14/47* (2013.01); *C07K 14/705* (2013.01); *C12N 7/00* (2013.01); *C12N 15/625* (2013.01); *C12N 15/86* (2013.01); *A61K 38/00* (2013.01); *C12N 2710/10322* (2013.01); *C12N 2710/10342* (2013.01); *C12N 2830/008* (2013.01)

(58) Field of Classification Search
None
See application file for complete search history.

(56) References Cited

U.S. PATENT DOCUMENTS 6,262,026 B1 *   7/2001   Heartlein ............... C12N 15/62
                                                   514/1.2

OTHER PUBLICATIONS

Leggiero ("Helper-Dependent Adenoviral Vector Expressing MLDLR/MTF fusion protein under the control of a muscle specific promoter for the treatment of FH", S23-S24, 32U Congresso Nazionale, Societa' Italiana Per Lo Studio Del L'aterosclerosi, Bologna Italy, 2018) (Year: 2018).*

* cited by examiner

*Primary Examiner* — Robert J Yamasaki
*Assistant Examiner* — Charles Zoltan Constantine
(74) *Attorney, Agent, or Firm* — Thomas | Horstmeyer, LLP

(57) ABSTRACT

A human chimeric protein(1) is described, expressed by a viral vector (2) designed for treating patients affected by genetic disorders, composed of a first cDNA sequence [SEQ. 2] of a N-terminal extracellular portion of a human receptor (4) of low-density lipoproteins (5) (hLDLR), fused with a second cDNA sequence [SEQ. 3] of the human transferrin (7) (hTf).

7 Claims, 6 Drawing Sheets
Specification includes a Sequence Listing.

CHIMERIC PROTEIN AND RELATED GENIC TRANSFER TECHNOLOGY

This application contains a sequence listing filed in electronic form as an ASCII.txt file entitled "321607-1010 Sequence Listing" having 28,326 bytes. The content of the sequence listing is incorporated herein in its entirety.

The present invention refers to a chimeric protein for treating patients affected by genetic disorders, in particular genetic lyspidemias. The present invention further refers to a genic transfer technology for the generation of a chimeric protein.

As known, the family hypercholesterolaemia (FH) is the most frequent among the genetic causes of dislipidemia, the most important factor responsible for an early coronary heart disease; this pathology is characterized by high levels of cholesterol which accumulates in the arterial walls, causing atheromas which can bring about an ischemia. Pharmacologic therapies are known for treating such pathologies, which imply a pharmacologic treatment for the whole life of a patient. For such purpose, in the '90s, an approach has been attempted with a genic therapy ex vivo for a FH with a retroviral vector, which brought about disappointing results that, though having precluded a further clinical development of the ex vivo approach, have confirmed the feasibility and the safety of the genic therapy LDLR in human beings (Grossman M, et al 1995). A number of different transgenic vectors and constructs have been tested afterwards in a pre-clinical environment; however, none has reached a stable genica expression with long-lasting metabolic effects (Van Craeyveld AND. et al 2011). In the 1a test years, different approaches have been developed with a genic therapy for FH, consisting in the endovenous administration of viral vectors which infect hepatocytes and allow the hepatic expression of therapeutic transgenes. These approaches however have a potential toxicity, which would not make them safe in a possible clinical use: therefore, the development of strategies to improve the expression of the transgene and reduce at a minimum the immune response is currently being enacted (Ezim A. et al 2016). The administrations of vectors for the production of therapeutic proteins in more accessible tissues, such as for example a muscle, would induce a lower systemic inflammatory response and would represent a certainly safer approach from a clinical point of view (Jenny A. Greig, 2016). Solutions are also known which are adapted to lower the level of cholesterol, as disclosed in the following patent documents: KR20160091276, CN105037554, US2013017250, EP0640620 and aimed for treating dyslipidemia, as disclosed in the following patent documents: WO9916458, RU2127115. A plurality of patent documents are also known, related to the treatment of such genetic disorders, characterized by the use of:
- a plurality of polypeptides secreted in combination with membrane vesicles, as disclosed in US2012321653;
- a polynucleotide codifying a chimeric protein and the related vector comprising the polynucleotide, as disclosed in US2002110869;
- a modified chimeric monoclonal antibody, as disclosed in WO9114438;
- a plurality of recombining molecules, as disclosed in WO9211383; and
- a plurality of chimeric proteins, as disclosed in patent document WO9639510.

Extrinsic factors are known, such as for example diet, feeding, lived life style, etc. and intrinsic factors, such as genetic, hereditary factors, which contribute to the development of coronary heart diseases. In particular, the most known genetic hyperlipidemia is the family hypercholesterolaemia (FH), and is caused by mutations in the gene responsible for the codification for the receptor of the low-density lipoproteins LDL. The therapeutic options for homozygous patients FH are improved, but not yet ideal, leaving the prognosis of these patients undesirable.

It is clear how no genic transfer technologies are known for the production of efficient and safe chimeric proteins in the care of the genetic disorders.

The genic therapy technology disclosed in parent application IT201900000651 allows producing a murine chimeric protein which could not be used in clinical practice, because it has not a safety profile adapted for the administration in humans being a murine chimeric protein. It is also clear how currently a totally human protein is not known, with a safety profile suitable for an administration in humans.

Object of the present invention is solving the above prior art problems, by providing a human chimeric protein expressed by a viral vector for treating patients affected by genetic disorders.

A further object of the present invention is solving the above prior art problems by providing a murine chimeric protein expressed by a viral vector, for treating patients affected by genetic disorders.

Another object of the present invention is providing a genic transfer technology for the generation of a human chimeric protein.

A further object of the present invention is providing a genic transfer technology for the generation of a murine chimeric protein.

The above and other objects and advantages of the invention, as will appear from the following description, are obtained with a chimeric protein as claimed in claim 1. Moreover, the above and other objects and advantages of the invention are also obtained with a genic transfer technology as claimed in claims 5 and 6. Preferred embodiments and non-trivial variations of the present invention are the subject matter of the dependent claims.

It is intended that all enclosed claims are an integral part of the present description.

It will be immediately obvious that numerous variations and modifications (for example related to shape, sizes, arrangements and parts with equivalent functionality) can be made to what is described, without departing from the scope of the invention, as appears from the enclosed claims.

The present invention will be better described by some preferred embodiments thereof, provided as a non-limiting example, with reference to the enclosed drawings, in which.

Figure 1:
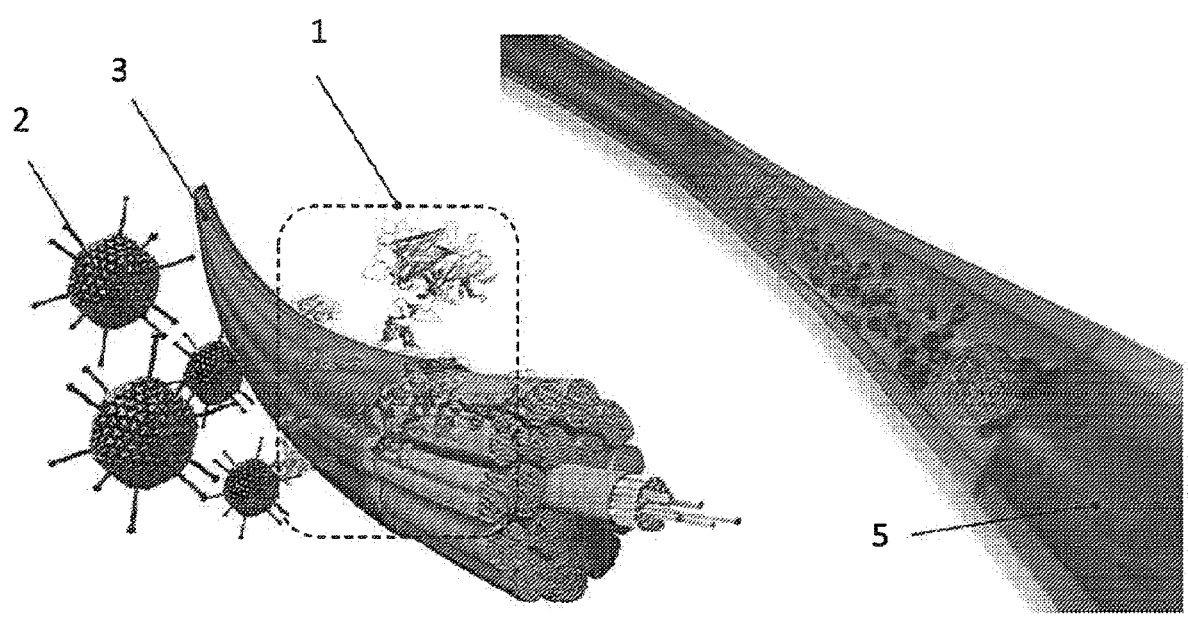
FIG. 1 shows a schematic representation of the genic transfer technology for the generation and administration of a chimeric protein according to the present invention.
Figure 2:
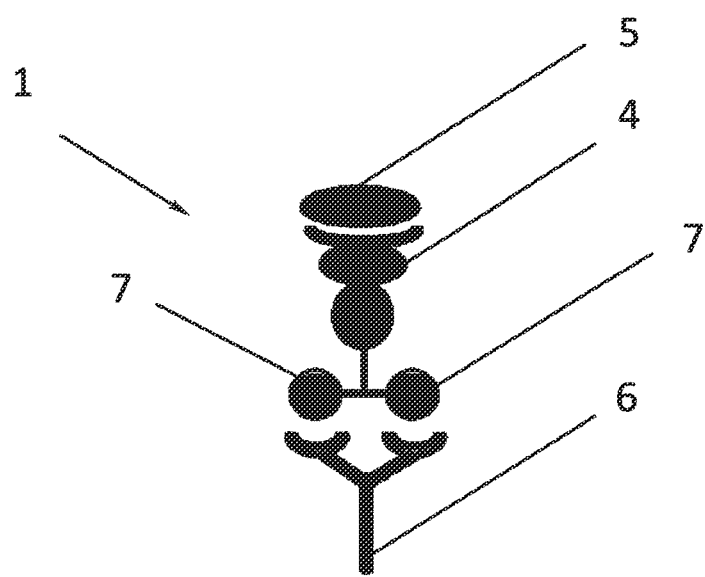
FIG. 2 shows a schematic representation of the viral vector which conveys the chimeric protein according to the present invention.

With reference to the Figures, a human chimeric protein 1 according to the present invention is described, depending on its amino acid and post-translational variations, which is composed of a first cDNA sequence [SEQ. 2] of a portion of the human receptor 4 of low-density lipoproteins 5 (hLDLR), and of a second cDNA sequence [SEQ. 3] of human transferrin 7 (hTf) fused with the cDNA sequence

[SEQ. 2] of the portion of the human receptor 4 of the low-density lipoproteins 5 (hLDLR).

This human chimeric protein 1, such as, for example, hLDLR-HTf, as function of its amino acid and post-translational variations, is designed for binding and removing from the blood flow the low-density lipoproteins 5 (LDL) circulating therein, by mediating their interiorization, through endocytosis, through the interaction of a receptor 6 (TfR1,TfR2) of the human transferrin 7 (hTf); in particular, such human chimeric protein 1 is designed for the intra-muscular administration 3 in humans, allowing a safer and more efficient clinical application, and allowing an efficient treatment of patients affected by genetic disorders, such as, for example, genetic lyspidemias, or other similar ones.

Advantageously, the human chimeric protein 1 is expressed by a viral vector 2, such as, for example, a retroviral, or adeno-associated, or adeno-viral vector, or an helper-dependent adenoviral vector (Hd-Ad), or other similar one, designed to enable such intra-muscular administration 3 of the human chimeric protein 1, guaranteeing a more efficient clinical application, reducing the risks normally associated with the systemic administration of viral vectors.

To enable a muscle-specific expression of the human chimeric protein 1, a first expression cassette has been designed, such as a minimum transcriptional unit, conveyed by the viral vector 2, enabling its intra-muscular administration 3, characterized by a DNA sequence [SEQ.5] comprising:

a DNA sequence [SEQ. 1] of a muscular promoter such as, for example, a promoter of the creatin kinasi (mCK) or other similar one, designed to activate a transcription of the human chimeric protein 1 and to guide its muscle-specific expression:

```
[SEQ. 1, SEQ ID NO: 1]
TCGAGGGCGCGCCGCGGCCGCTCTTTGTAATGAAAAAAAAAAAAAAAAGGTCAGGGCCAGG
CATGGTGACTGGGGCCTTTAATTCCAGCATTCCAGGAGGCAGAGCCAAGAGGATCTCTGTG
AGTTCAAGGCCATCCTGGTCTATAGAGAGAGTTCCAGAACAGCCAGGGCTACAGATAAACC
CATCTGGAAAAACAAAGTTGAATGACCCAAGAGGGGTTCTCAGAGGGTGGCGTGTGCTCCC
TGGCAAGCCTATGACATGGCCGGGGCCTGCCTCTCTCTGCCTCTGACCCTCAGTGGCTCCC
ATGAACTCCTTGCCCAATGGCATCTTTTTCCTGCGCTCCTTGGGTTATTCCAGTCTCCCCT
CAGCATTCCTTCCTCAGGGCCTCGCTCTTCTCTGCTCCCTCCTTGCACAGCTGGCTCTG
TCCACCTCAGATGTCACAGTGCTCTCTCAGAGGAGGAAGGCACCATGTACCCTCTGTTTCC
CAGGTAAGGGTTCAATTTTTAAAAATGGTTTTTTGTTTGTTTGTTTGTTTGTTTGTTTGTT
TGTTTTTCAAGACAGGGCTCCTCTGTGTAGTCCTAACTGTCTTGAAACTCCCTCTGTAGAC
CAGGTCGACCTCGAACTCTTGAAACCTGCCACGGACCACCCAGTCAGGTATGGAGGTCCCT
GGAATGAGCGTCCTCGAAGCTAGGTGGGTAAGGGTTCGGCGGTGACAAACAGAAACAAACA
CAGAGGCAGTTTGAATCTGAGTGTATTTTGCAGCTCTCAAGCAGGGGATTTTATACATAAA
AAAAAAAAAAAAAAAAAAACCAAACATTACATCTCTTAGAAACTATATCCAATGAAACAAT
CACAGATACCAACCAAAACCATTGGGCAGAGTAAAGCACAAAAATCATCCAAGCATTACAA
CTCTGAAACCATGTATTCAGTGAATCACAAACAGAACAGGTAACATCATTATTAATATAAA
TCACCAAAATATAACAATTCTAAAAGGATGTATCCAGTGGGGGCTGTCGTCCAAGGCTAGT
GGCAGATTTCCAGGAGCAGGTTAGTAAATCTTAACCACTGAACTAACTCTCCAGCCCCATG
GTCAATTATTATTTAGCATCTAGTGCCTAATTTTTTTTATAAATCTTCACTATGTAATTT
AAAACTATTTTAATTCTTCCTAATTAAGGCTTTCTTTACCATATACCAAAATTCACCTCCA
ATGACACACGCGTAGCCATATGAAATTTTATTGTTGGGAAAATTTGTACCTATCATAATAG
TTTTGTAAATGATTTAAAAAGCAAAGTGTTAGCCGGGCGTGGTGGCACACGCCTTTAATCC
CTGCACTCGGGAGGCAGGGCAGGAGGATTTCTGAGTTTGAGGCCAGCCTGGTCTACAGAG
TGAGTTCCAGGACAGCCAGGGCTACACAGAGAAACCCTGTCTCGAACCCCCCACCCCCCAA
AAAAAGCAAAGTGTTGGTTTCCTTGGGGATAAAGTCATGTTAGTGGCCCATCTCTAGGCCC
ATCTCACCCATTATTCTCGCTTAAGATCTTGGCCTAGGCTACCAGGAACATGTAAATAAGA
AAAGGAATAAGAGAAAACAAAACAGAGAGATTGCCATGAGAACTACGGCTCAATATTTTTT
CTCTCCGGCGAAGAGTTCCACAACCATCTCCAGGAGGCCTCCACGTTTTGAGGTCAATGGC
CTCAGTCTGTGGAACTTGTCACACAGATCTTACTGGAGGTGGTGTGGCAGAAACCCATTCC
```

-continued

```
TTTTAGTGTCTTGGGCTAAAAGTAAAAGGCCCAGAGGAGGCCTTTGCTCATCTGACCATGC
TGACAAGGAACACGGGTGCCAGGACAGAGGCTGGACCCCAGGAACACCTTAAACACTTCTT
CCCTTCTCCGCCCCCTAGAGCAGGCTCCCCTCACCAGCCTGGGCAGAAATGGGGAAGATG
GAGTGAAGCCATACTGGCTACTCCAGAATCAACAGAGGGAGCCGGGGGCAATACTGGAGAA
GCTGGTCTCCCCCCAGGGGCAATCCTGGCACCTCCCAGGCAGAAGAGGAAACTTCCACAGT
GCATCTCACTTCCATGAATCCCCTCCTCGGACTCTGAGGTCCTTGGTCACAGCTGAGGTGC
AAAAGGCTCCTGTCATATTGTGTCCTGCTCTGGTCTGCCTTCACAGCTTGGGGGCCACCTA
GCCCACCTCTCCCTAGGGATGAGAGCAGCCACTATGGGTCTAGGCTGCCCATGTAAGGAGG
CAAGGCCTGGGGACACCCGAGATGCCTGGTTATAATTAACCCAGACATGTGGCTGCTCCCC
CCCCCCAACACCTGCTGCCTGAGCCTCACCCCCACCCCGGTGCCTGGGTCTTAGGCTCTGT
ACACCATGGAGGAGAAGCTCGCTCTAAAAATAACCCTGTCCCTGGTGGATCCAGGGTGGAG
GGGCAGGCTGAGGGCGGCCACTTCCCTCAGCCGCAGTTTGTTTTCCCAAGAATGGTTTTTC
TGCTTCTGTAGCTTTTCCTGTCAATTCTGCCATGGTGGAGCAGCCTGCACTGGGCTTCTGG
GAGAAACCAAACCGGGTTCTAACCTTTCAGCTACAGTCATTGCCTTTCCTGTAGATGGGCG
ACTACAGCCCCACCCCCACCCCCGTCTCCTGTATCCTTCCTGGGCCTGGGGATCCTAGGCT
TTCACTGGAAATTTCCCCCCAGGTGCTGTAGGCTAGAGTCACGGCTCCCAAGAACAGTGCT
TGCCTGGCATGCATGGTTCTGAACCTCCAACTGCAAAAAATGACACATACCTTGACCCTTG
GAAGGCTGAGGCAGGGGGATTGCCATGAGTGCAAAGCCAGACTGGGTGGCATAGTTAGACC
CTGTCTCAAAAAACCAAAAACAATTAAATAACTAAAGTCAGGCAAGTAATCCTACTCAGGA
GACTGAGGCAGAGGGATTGTTACATGTCTGAGGCCAGCCTGGACTACATAGGGTTTCAGGC
TAGCCCTGTCTACAGAGTAAGGCCCTATTTCAAAAACACAAACAAAATGGTTCTCCCAGCT
GCTAATGCTCACCAGGCAATGAAGCCTGGTGAGCATTAGCAATGAAGGCAATGAAGGAGGG
TGCTGGCTACATCAGGCGTGTGGGGACTGAGGGCAGGCTGTAACAGGCTTGGGGGCCAGGG
CTTATACGTGCCTGGGACTCCCAAAGTATTACTGTTCCATGTTCCCGGCGAAGGGCCAGCT
GTCCCCCGCCAGCTAGACTCAGCACTTAGTTTAGGAACCAGTGAGCAAGTCAGCCCTTGGG
GCAGCCCATACAAGGCCATGGGCTGGGCAAGCTGCACGCCTGGGTCCGGGGTGGGCACGG
TGCCCGGGCAACGAGCTGAAAGCTCATCTGCTCTCAGGGGCCCCTCCCTGGGGACAGCCCC
TCCTGGCTAGTCACACCCTGTAGGCTCCTCTATATAACCCAGGGGCACAGGGGCTGCCCCC
GGGTCACCACCACCTCCACAGCACAGACAGACACTCAGGAGCCAGCCAGCCAGGTAGGGAC
TGAGAGAAATCACTGGGGTGGGAGTGGGGCGTGGGAGTCCAAGGGTCTGCTCACCCAGTCA
TGTTATGGTTGTGGATTTTGCAGCACAAGTTGTGGGACAAATGTCTGGGACACCTAGGTC
TCAATAGCCACCAAGTGTCCCCTCCTTGCAAGGCAGGGTGGGCTGGAACTTAGTTTAGCAG
AGTTAATGGCCCACACAAAGACAGTTGTCTCAGTGACACCTGTCAGTGGCCCCTTTAACTTT
GTAACCATGTGGACCTGTGTTGCAGCTCTGTGACCTTGTGTCTCACTGTCCTGGTCTGTCT
CTATGTCTCTCTGTCTCTCTGTCTCTATCTCTCTTTCTGTCTCTCTCTCTCCCTCTCTC
TTTCGAGATGGGTCAGGGGGGGTGGTGTTCTCTGCATAGCCCTGGCTGTCCTGGAACTCA
CTCTGTAGACCAGCCTGGCCTCGAACTCAGAAATCCACCTGCCTCCCAAGTGCTGGGATTA
AAGGCGTGTGCCACCACCGCCCGGCGGGTCTTTCTTGTGTGAGACTTGGGGGCTCTCACTC
TTACAGGCCCCTGGCTTTCCTTTGAGTCCTTCTGTCTGGCTGTCTCTGGGATCTTGAAGGC
AGGAAGGACTACATGACTCAGTTTACCTGGAGATCTTAGAGAATCTGTGATGAGTTTGGGG
ATTCCGAAGCTTTCTGCTTCTGCGTCTTGCCTCGGTGTCCTGTCTCCTGGGGTGCCCCTGA
```

-continued

```
GGGAGGGGGTAGCAGAGGATACAGAACCTTCTGAAGGGAGAGATCTGGGCTGGGAGCCCGG

GGTGTCCTTGAGGCCCAGAGCCTGGCTGTGTGTCCTCCTGGCCACCCCAGCCCACCTGTCC

CAATGCTGACTTAGTGCAAGGCGAGCCAGCAAGGAGGGAGGACAGGTGGCAGTGGGGGGTG

AGGAGCATCTAAAAATAGCCACAAAGTAGCAGCTTCAAGGGCTTTGGGTCTCTGTCTGCCC

CACACTCTTCTCTCAGCTTGGTCCACCTTCCCTCTCACCTTCCTCTGAGGCCCCCTTCCAG

CCCCGATGGAGGCCTGATGTCCCCCATGGTCAGTGCTTCAGGGATCTAGTCAATAAAATTA

ATAATGAAAAACAACAGTAATAAAATACACGTGACGTGACTGGGGCAGCTTAGGGCTTAGT

TCAAATCCCAGTGTTCACACCCTTTAAAAGACAAGACAAAACAAAACAGCTGGCTGTGGGG

GAGAACATCAGAATCCCCCTGGGGAGGTGGGGACAGGGGATCTGTGGGGCTCCATGGCCAG

CCAGCCTAGCTCCAGGCCTGCGAGAGACCCTACCTCAAGATAAAAATAAAATAAAATAAAA

TAAATATATAAAATAACAATCTTGCAGCACCTGAGGTCACCACTGGAATGTGCACACCTGT

GCACATACATGAGCCTGCACTACAAACAAAAATATTAACAGTAACTGTTAGAATCCCAGCT

GCAACTTCATGCCAGGTGCCAGGTCCATGCTCATCAGTCAGGGACTGGAACTCAGAGATCT

CCTGGGAAAGCTTCAGTCTCACAGATTCAAAAGCCAGAGAGATCTAGTCACAGCCTGGGGC

CCAGAGCAGTGACTTAGGAGAGCCGTGCCTTTTAAAGTGGACCTTGTAGACAGCCAGAGGT

GGAGGGACTGGGAGAAGTGGCTGAAGCCTCCAGACTCATTCCCACGCCCACATCTGGACTA

ATTTGGATCAGAATCTCAGGGGAGCCCTTATGGCTTTTCTCAGGTGTGCACATATAATCTT

TACCAGGGTCCTCACACAGAGCCTGTCAGATTGGTTTTCAATTTCTGTGACAAACACCATG

ACCAAGACAACCTAGAAAAGAGAAAGCATTAATTTGGGGCTCAGGGTTCTGGAGCGGCAGG

GAGGTGGGCATGGTGCTGGAGCAGAGGCTGGAAGCTCACATCTTTATCAACAACCAGAGGC

AGTGAGAGCCACTTGGGAATGGGGTGGCTTTTCGGAAATCTCAAAGCCCACAAGCAATGGC

ACACCTCCTCCAACAAGGCCACACCTCCGAATCCTTCCCAAACAGTTCCACCGACTGGGGA

CCAAACATTCAAATATGTGAGTCTGAGGCTCTTCTCATTCAAATCACCACAGACCCAAGAA

CAATCGAATAAAATATTTGTGTTATGTGCCAGGCACTGGCCGAGGCGCTTTTCTTGTCTTT

TAATCCCTCCCAAGAGGTCAGCGATGCCACAGTCTCCATGTTACAGATGAGTGAACAGGAA

AGTCAAACAGGCTCCTCAGAGTCACGCGGCTGCTTGTAAGTTGCAAAGCCGAAATTCGAAC

CCAGACCATCTGATCCAGATCCTTTGCTGCTTTTATTCATCTTTTTATTTTATTTTATTTT

ATTTTAATTCCTGGTGGCAGGGTTTCTGTAGCCCAGGCTACCCTTGAATTCACTGCAATCC

TCCTGCCTCAGTTTCAGAGTGTTGGAATTACAAGCATGGACCATCATGCCCAGTTCCTTTG

GGTTGAGATAGAGACCTGTGTAGGAGCCCAGACTCGGGCTGGTCTCCAGCTCTCTACGTAG

ATGAAGATGACCTTGAACTGCTGGGATTTCAGGCATGAGCAGCCACACCCAGATTTGCTGA

GCGCCAAACTGTTACCCAGGGTCCTAAGCTTGCTGGGCAAGCACTCTGCCAGCAGAACCCC

AGCCCCAGATCCTGTATTTTTGTAGTTGTTTTTGTTTATGTGACTGTCCTTTTCTGGCTTT

AGACAAAAGGTTTTGCCCTCCTTTTCCAGCTAGAGAGACTGAGTCCCCAGCAGGATCACAT

AGGCAGGATGTGGCCACATCAGGCAACTTGGGCTCCTGATGTTTCCTTGCAAGGCTGAGGT

TCACAGGGGGAGAACCCCCCTTTTTCAAGCCCACGGTCCGACGGACTGCAAGCCCCCAGCA

ACTGAGTTCTTAAGTCTGAGCGGCCGCACCCGGTCTGCTCGCAGGGTCCCAAAGGCCGCCA

CCCTCGACTCTGGCTAACTAGAGAACCCACTGCTTACTGGCTTATCGAAATTAATACGACT

CACTATAGGGAGACCCAAGCTTGGTACCGAGCTCGGATCCAGCC
``` the following first cDNA sequence [SEQ. 2] of the portion of the human receptor 4 of the low-density lipoproteins 5 (hLDLR) of the human chimeric protein 1:

[SEQ. 2, SEQ ID NO:]
```
ATGGGGCCCTGGGGCTGGAAATTGCGCTGGACCGTCGCCTTGCTCCTCGCCGCGGCGGGGA

CTGCAGTGGGCGACAGATGTGAAAGAAACGAGTTCCAGTGCCAAGACGGGAAATGCATCTC

CTACAAGTGGGTCTGCGATGGCAGCGCTGAGTGCCAGGATGGCTCTGATGAGTCCCAGGAG

ACGTGCTTGTCTGTCACCTGCAAATCCGGGGACTTCAGCTGTGGGGCCGTGTCAACCGCT

GCATTCCTCAGTTCTGGAGGTGCGATGGCCAAGTGGACTGCGACAACGGCTCAGACGAGCA

AGGCTGTCCCCCCAAGACGTGCTCCCAGGACGAGTTTCGCTGCCACGATGGGAAGTGCATC

TCTCGGCAGTTCGTCTGTGACTCAGACCGGGACTGCTTGGACGGCTCAGACGAGGCCTCCT

GCCCGGTGCTCACCTGTGGTCCCGCCAGCTTCCAGTGCAACAGCTCCACCTGCATCCCCCA

GCTGTGGGCCTGCGACAACGACCCCGACTGCGAAGATGGCTCGGATGAGTGGCCGCAGCGC

TGTAGGGGTCTTTACGTGTTCCAAGGGGACAGTAGCCCCTGCTCGGCCTTCGAGTTCCACT

GCCTAAGTGGCGAGTGCATCCACTCCAGCTGGCGCTGTGATGGTGGCCCCGACTGCAAGGA

CAAATCTGACGAGGAAAACTGCGCTGTGGCCACCTGTCGCCCTGACGAATTCCAGTGCTCT

GATGGAAACTGCATCCATGGCAGCCGGCAGTGTGACCGGGAATATGACTGCAAGGACATGA

GCGATGAAGTTGGCTGCGTTAATGTGACACTCTGCGAGGGACCCAACAAGTTCAAGTGTCA

CAGCGGCGAATGCATCACCCTGGACAAAGTCTGCAACATGGCTAGAGACTGCCGGGACTGG

TCAGATGAACCCATCAAAGAGTGCGGGACCAACGAATGCTTGGACAACAACGGCGGCTGTT

CCCACGTCTGCAATGACCTTAAGATCGGCTACGAGTGCCTGTGCCCCGACGGCTTCCAGCT

GGTGGCCCAGCGAAGATGCGAAGATATCGATGAGTGTCAGGATCCCGACACCTGCAGCCAG

CTCTGCGTGAACCTGGAGGGTGGCTACAAGTGCCAGTGTGAGGAAGGCTTCCAGCTGGACC

CCCACACGAAGGCCTGCAAGGCTGTGGGCTCCATCGCCTACCTCTTCTTCACCAACCGGCA

CGAGGTCAGGAAGATGACGCTGGACCGGAGCGAGTACACCAGCCTCATCCCCAACCTGAGG

AACGTGGTCGCTCTGGACACGGAGGTGGCCAGCAATAGAATCTACTGGTCTGACCTGTCCC

AGAGAATGATCTGCAGCACCCAGCTTGACAGAGCCCACGGCGTCTCTTCCTATGACACCGT

CATCAGCAGGGACATCCAGGCCCCCGACGGGCTGGCTGTGGACTGGATCCACAGCAACATC

TACTGGACCGACTCTGTCCTGGGCACTGTCTCTGTTGCGGATACCAAGGGCGTGAAGAGGA

AAACGTTATTCAGGGAGAACGGCTCCAAGCCAAGGGCCATCGTGGTGGATCCTGTTCATGG

CTTCATGTACTGGACTGACTGGGGAACTCCCGCCAAGATCAAGAAAGGGGGCCTGAATGGT

GTGGACATCTACTCGCTGGTGACTGAAAACATTCAGTGGCCCAATGGCATCACCCTAGATC

TCCTCAGTGGCCGCCTCTACTGGGTTGACTCCAAACTTCACTCCATCTCAAGCATCGATGT

CAATGGGGGCAACCGGAAGACCATCTTGGAGGATGAAAAGAGGCTGGCCCACCCCTTCTCC

TTGGCCGTCTTTGAGGACAAAGTATTTTGGACAGATATCATCAACGAAGCCATTTTCAGTG

CCAACCGCCTCACAGGTTCCGATGTCAACTTGTTGGCTGAAAACCTACTGTCCCCAGAGGA

TATGGTCCTCTTCCACAACCTCACCCAGCCAAGAGGAGTGAACTGGTGTGAGAGGACCACC

CTGAGCAATGGCGGCTGCCAGTATCTGTGCCTCCCTGCCCCGCAGATCAACCCCCACTCGC

CCAAGTTTACCTGCGCCTGCCCGGACGGCATGCTGCTGGCCAGGGACATGAGGAGCTGCCT

CACAGAGGCTGAGGCTGCAGTGGCCACCCAGGAGACATCCACCGTCAGGCTAAAGGTCAGC

TCCACAGCCGTAAGGACACAGCACACAACCACCCGGCCTGTTCCCGACACCTCCCGGCTGC

CTGGGGCCACCCCTGGGCTCACCACGGTGGAGATAGTGACAATGTCTCACCAA.
``` and the following second cDNA sequence [SEQ. 3] of the human transferrin 7 (hTf) of the human chimeric protein 1:

[SEQ. 3, SEQ ID NO: 3]
ATGAGGCTCGCCGTGGGAGCCCTGCTGGTCTGCGCCGTCCTGGGGCTGTGTCTGGCTGTCC

CTGATAAAACTGTGAGATGGTGTGCAGTGTCGGAGCATGAGGCCACTAAGTGCCAGAGTTT

CCGCGACCATATGAAAAGCGTCATTCCATCCGATGGTCCCAGTGTTGCTTGTGTGAAGAAA

GCCTCCTACCTTGATTGCATCAGGGCCATTGCGGCAAACGAAGCGGATGCTGTGACACTGG

ATGCAGGTTTGGTGTATGATGCTTACCTGGCTCCCAATAACCTGAAGCCTGTGGTGGCAGA

GTTCTATGGGTCAAAAGAGGATCCACAGACTTTCTATTATGCTGTTGCTGTGGTGAAGAAG

GATAGTGGCTTCCAGATGAACCAGCTTCGAGGCAAGAAGTCCTGCCACACGGGTCTAGGCA

GGTCCGCTGGGTGGAACATCCCCATAGGCTTACTTTACTGTGACTTACCTGAGCCACGTAA

ACCTCTTGAGAAAGCAGTGGCCAATTTCTTCTCGGGCAGCTGTGCCCCTTGTGCGGATGGG

ACGGACTTCCCCCAGCTGTGTCAACTGTGTCCAGGGTGTGGCTGCTCCACCCTTAACCAAT

ACTTCGGCTACTCGGGAGCCTTCAAGTGTCTGAAGGATGGTGCTGGGGATGTGGCCTTTGT

CAAGCACTCGACTATATTTGAGAACTTGGCAAACAAGGCTGACAGGGACCAGTATGAGCTG

CTTTGCCTGGACAACACCCGGAAGCCGGTAGATGAATACAAGGACTGCCACTTGGCCCAGG

TCCCTTCTCATACCGTCGTGGCCCGAAGTATGGGCGGCAAGGAGGACTTGATCTGGGAGCT

TCTCAACCAGGCCCAGGAACATTTTGGCAAAGACAAATCAAAAGAATTCCAACTATTCAGC

TCTCCTCATGGGAAGGACCTGCTGTTTAAGGACTCTGCCCACGGGTTTTTAAAAGTCCCCC

CCAGGATGGATGCCAAGATGTACCTGGGCTATGAGTATGTCACTGCCATCCGGAATCTACG

GGAAGGCACATGCCCAGAAGCCCCAACAGATGAATGCAAGCCTGTGAAGTGGTGTGCGCTG

AGCCACCACGAGAGGCTCAAGTGTGATGAGTGGAGTGTTAACAGTGTAGGGAAAATAGAGT

GTGTATCAGCAGAGACCACCGAAGACTGCATCGCCAAGATCATGAATGGAGAAGCTGATGC

CATGAGCTTGGATGGAGGGTTTGTCTACATAGCGGGCAAGTGTGGTCTGGTGCCTGTCTTG

GCAGAAAACTACAATAAGAGCGATAATTGTGAGGATACACCAGAGGCAGGGTATTTTGCTA

TAGCAGTGGTGAAGAAATCAGCTTCTGACCTCACCTGGGACAATCTGAAAGGCAAGAAGTC

CTGCCATACGGCAGTTGGCAGAACCGCTGGCTGGAACATCCCCATGGGCCTGCTCTACAAT

AAGATCAACCACTGCAGATTTGATGAATTTTTCAGTGAAGGTTGTGCCCCTGGGTCTAAGA

AAGACTCCAGTCTCTGTAAGCTGTGTATGGGCTCAGGCCTAAACCTGTGTGAACCCAACAA

CAAAGAGGGATACTACGGCTACACAGGCGCTTTCAGGTGTCTGGTTGAGAAGGGAGATGTG

GCCTTTGTGAAACACCAGACTGTCCCACAGAACACTGGGGGAAAAAACCCTGATCCATGGG

CTAAGAATCTGAATGAAAAGACTATGAGTTGCTGTGCCTTGATGGTACCAGGAAACCTGT

GGAGGAGTATGCGAACTGCCACCTGGCCAGAGCCCCGAATCACGCTGTGGTCACACGGAAA

GATAAGGAAGCTTGCGTCCACAAGATATTACGTCAACAGCAGCACCTATTTGGAAGCAACG

TAACTGACTGCTCGGGCAACTTTTGTTTGTTCCGGTCGGAAACCAAGGACCTTCTGTTCAG

AGATGACACAGTATGTTTGGCCAAACTTCATGACAGAAACACATATGAAAAATACTTAGGA

GAAGAATATGTCAAGGCTGTTGGTAACCTGAGAAAATGCTCCACCTCATCACTCCTGGAAG

CCTGCACTTTCCGTAGACCTTAA a polyadenylation signal designed for the termination of the transcription of the human chimeric protein 1, in particular the following DNA sequence [SEQ. 4] composed of a first, post-transcriptional regulatory element of the Woodchuck hepatitis WPRE virus, designed to increase the amount of non-implanted nuclear and cytoplasmic RNA, positively affecting the amount of human chimeric protein 1 produced, and of a second regulatory element of the Simian Virus 40 PolyA in its antisense orientation, designed to induce a stronger genic expression:

```
[SEQ. 4, SEQ ID NO: 4]
AATCAACCTCTGGATTACAAAATTTGTGAAAGATTGACTGGTATTCTTAACTATGTTGCTC

CTTTTACGCTATGTGGATACGCTGCTTTAATGCCTTTGTATCATGCTATTGCTTCCCGTAT

GGCTTTCATTTTCTCCTCCTTGTATAAATCCTGGTTGCTGTCTCTTTATGAGGAGTTGTGG

CCCGTTGTCAGGCAACGTGGCGTGGTGTGCACTGTGTTTGCTGACGCAACCCCCACTGGTT

GGGGCATTGCCACCACCTGTCAGCTCCTTTCCGGGACTTTCGCTTTCCCCCTCCCTATTGC

CACGGCGGAACTCATCGCCGCCTGCCTTGCCCGCTGCTGGACAGGGGCTCGGCTGTTGGGC

ACTGACAATTCCGTGGTGTTGTCGGGGAAGCTGACGTCCTTTCCATGGCTGCTCGCCTGTG

TTGCCACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTTCGC

CCTCAGACGAGTCGGATCTCCCTTTGGGCCGCCTCCCCGCCTGTTTCGCCTCGGCGTCCGG

TCCGTGTTGCTTGGTCTTCACCTGTGCAGACTTGCGAACCATGGATTCCACCGTGAACTTT

GTCTCCTGGCATGCAAATCGTCAACTTGGCATGCCAAGTGAAAAAAATGCTTTATTTGTGA

AATTTGTGATGCTATTGCTTTATTTGTAACCATTATAAGCTGCAATAAACAAGTTAACAAC

AACAATTGCATTCATTTTATGTTTCAGGTTCAGGGCATATGGAGCTGGCGCGCC.
```

The viral vector 2 of the human chimeric protein 1, designed to convey the first expression cassette and to enable an intra-muscular administration 3 of the human chimeric protein 1, is preferably an adenoviral vector of the helper-dependent type (HD-AdlmCKhLDLR-hTf), and is generated through an introduction of the expression cassette into a first plasmid (pLPBL1) and subcloning the expression cassette in un second plasmid containing a viral structure (pΔ21), through ligation in the restriction site (AscI).

Moreover, the first cDNA sequence [SEQ. 2] and the second cDNA sequence [SEQ. 3] of the human chimeric protein 1 are converted during the biologic processes of translation and transcription in the following succession of amino acids [PR. 1] of the human chimeric protein 1:

```
[PR. 1, SEQ ID NO: 5]
MGPWGWKLRWTVALLLAAAGTAVGDRCERNEFQCQDGKCISYKWVCDGSAECQDGSDESQE

TCLSVTCKSGDFSCGGRVNRCIPQFWRCDGQVDCDNGSDEQGCPPKTCSQDEFRCHDGKCI

SRQFVCDSDRDCLDGSDEASCPVLTCGPASFQCNSSTCIPQLWACDNDPDCEDGSDEWPQR

CRGLYVFQGDSSPCSAFEFHCLSGECIHSSWRCDGGPDCKDKSDEENCAVATCRPDEFQCS

DGNCIHGSRQCDREYDCKDMSDEVGCVNVTLCEGPNKFKCHSGECITLDKVCNMARDCRDW

SDEPIKECGTNECLDNNGGCSHVCNDLKIGYECLCPDGFQLVAQRRCEDIDECQDPDTCSQ

LCVNLEGGYKCQCEEGFQLDPHTKACKAVGSIAYLFFTNRHEVRKMTLDRSEYTSLIPNLR

NVVALDTEVASNRIYWSDLSQRMICSTQLDRAHGVSSYDTVISRDIQAPDGLAVDWIHSNI

YWTDSVLGTVSVADTKGVKRKTLFRENGSKPRAIVVDPVHGFMYWTDWGTPAKIKKGGLNG

VDIYSLVTENIQWPNGITLDLLSGRLYWVDSKLHSISSIDVNGGNRKTILEDEKRLAHPFS

LAVFEDKVFWTDIINEAIFSANRLTGSDVNLLAENLLSPEDMVLFHNLTQPRGVNWCERTT

LSNGGCQYLCLPAPQINPHSPKFTCACPDGMLLARDMRSCLTEAEAAVATQETSTVRLKVS
```

-continued

STAVRTQHTTTRPVPDTSRLPGATPGLTTVEIVTMSHQMRLAVGALLVCAVLGLCLAVPDK

TVRWCAVSEHEATKCQSFRDHMKSVIPSDGPSVACVKKASYLDCIRAIAANEADAVTLDAG

LVYDAYLAPNNLKPVVAEFYGSKEDPQTFYYAVAVVKKDSGFQMNQLRGKKSCHTGLGRSA

GWNIPIGLLYCDLPEPRKPLEKAVANFFSGSCAPCADGTDFPQLCQLCPGCGCSTLNQYFG

YSGAFKCLKDGAGDVAFVKHSTIFENLANKADRDQYELLCLDNTRKPVDEYKDCHLAQVPS

HTVVARSMGGKEDLIWELLNQAQEHEGKDKSKEFQLFSSPHGKDLLFKDSAHGFLKVPPRM

DAKMYLGYEYVTAIRNLREGTCPEAPTDECKPVKWCALSHHERLKCDEWSVNSVGKIECVS

AETTEDCIAKIMNGEADAMSLDGGFVYIAGKCGLVPVLAENYNKSDNCEDTPEAGYFAIAV

VKKSASDLTWDNLKGKKSCHTAVGRTAGWNIPMGLLYNKINHCRFDEFFSEGCAPGSKKDS

SLCKLCMGSGLNLCEPNNKEGYYGYTGAFRCLVEKGDVAFVKHQTVPQNTGGKNPDPWAKN

LNEKDYELLCLDGTRKPVEEYANCHLARAPNHAVVTRKDKEACVHKILRQQQHLFGSN

VTDCSGNFCLFRSETKDLLFRDDTVCLAKLHDRNTYEKYLGEEYVKAVGNLRKCSTSSLLE

ACTFRRP.

Moreover, a genic transfer technology designed for the generation and intra-muscular administration 3 of the human chimeric protein 1, for efficiently treating patients affected by genetic disorders, such as, for example, genetic lyspidemias or other similar ones, consists in the steps of:
generation of the first expression cassette;
generation of the viral vector 2 expressing the human chimeric protein 1;
intra-muscular administration 3 of the viral vector 2 expressing the human chimeric protein 1.

As the experimental results shown in Figures FIGS. 3-9 demonstrate, obtained both in vitro and in vivo related to the intra-muscular administration 3 of the human chimeric protein 1 through viral vector 2 and the related genic transfer technology in a murine model of family hypercholesterolaemia, the possibility of being used in the clinical practice and adapted to the administration in humans is confirmed.

Figure 3:
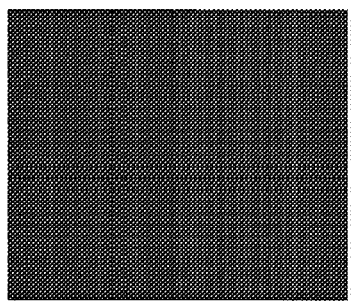
FIGS. 3-17 show evidences of experiments related to the expression in a murine model through the genic transfer technology of the chimeric protein according to the present invention.
Figure 4:
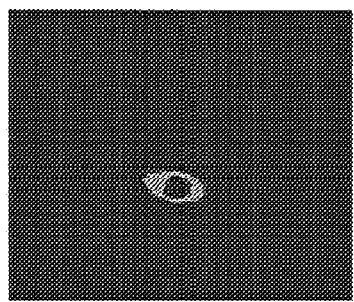
Figure 5:
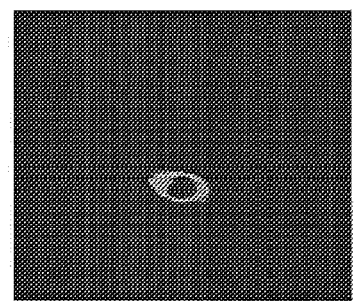
Figure 6:
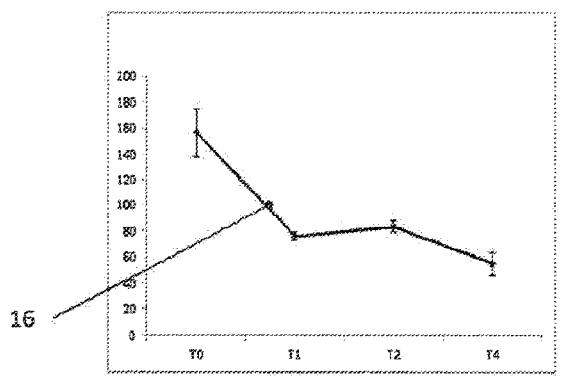
Figure 7:
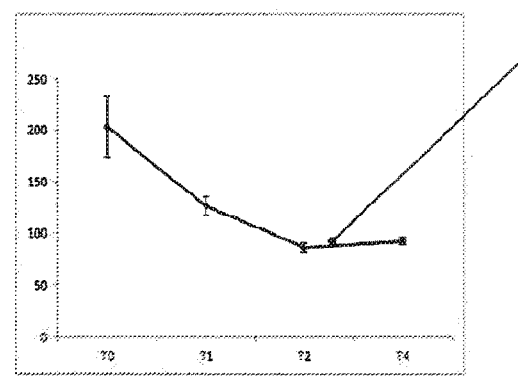
Figure 8:
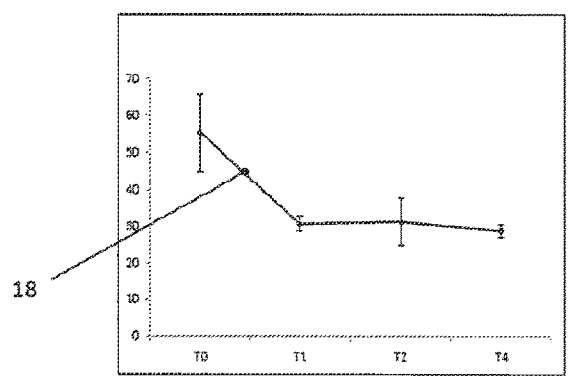
Figure 9:
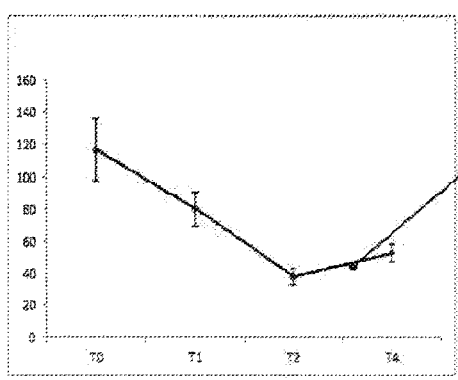

In particular, as shown in FIGS. 3, 4 and 5, a viral vector HD-AdMCK-hLDLRhTfR has been generated, expressing the human chimeric protein hLDLR-hTf, and infecting a plurality of muscular cells C2C12. After 48 hours from the infection, the supernatant has been collected. Such supernatant containing the human chimeric protein has been used to infect a cellular model of family hypercholesterolaemia, the CHOldlA7, missing cells of the receptor of the low-density lipoproteins LDL.

Through confocal microscopy, the capacity has bene evaluated of the human chimeric protein hLDLR-hTf of restoring the internalization of the low-density lipoproteins LDL marked in the cellular line CHOldlA7 lacking the receptor of the low-density lipoproteins hLDLR. In particular, FIG. 3 shows the image of cellular nuclei before the administration; FIG. 4 shows the image of cells CHOldlA7 after infection with the supernatant of the cells C2C12 infected with the viral vector HD-AdMCK-hLDLRhTF and after treatment with the low-density lipoproteins LDL marked with fluorescence with a concentration of 10 µg/ml for 5 hours; and FIG. 5 shows an overlapping of the cellular nuclei and of the LDL marked with fluorescence, pointing out that the cells CHOldlA7 have re-acquired the capability of incorporating the LDL.

Finally, FIGS. 6-9 show a progressive reduction of the total cholesterol (FIG. 7), HDL cholesterol (FIG. 8), LDL cholesterol (FIG. 9), triglycerides (FIG. 6), in a murine model of family hypercholesterolaemia, following the actuation of the genic transfer technology according to the present invention, through the following operating steps:
providing a first sample of cavies, such as, for example, mice, rats or other similar ones, deficient of the LDL receptor, treated with the viral vector expressing the human chimeric protein;
withdrawing a plurality of blood samples from the retrorbital plexus, from the first sample of cavies before administering the vector (time T0), one week after administration (time T1), two weeks after administration (time T2) and four weeks after administration (time T3);
determining with serum the total cholesterol 17, HDL cholesterol 18, LDL cholesterol 19, triglycerides 16, etc., pointing out a lowering of total cholesterol, HDL cholesterol, LDL cholesterol, triglycerides in the first sample of cavies.

Moreover, a genic transfer technology is described, for treating patients affected by genetic disorders, such as, for example, genetic lyspidemias or other similar ones, designed for the generation and intra-muscular administration 3 of a murine chimeric protein 10, expressed by the viral vector 2, designed to enable the intra-muscular administration 3 of the murine chimeric protein 10.

In particular, the murine chimeric protein 10 is designed to reduce the cholesterol of a plurality of low-density lipoproteins (LDL) in patients affected by genetic lyspidemias, binding such plurality of lipoproteins and generating their internalization in the cells, through intra-muscular administration 3. Such technology, according to the present invention, mainly comprises the steps of:
production of the viral vector 2;
possible development of a chemical modification 6, such as, for example, a PEGylation reaction on the viral vector 2, with a polyethylene glycol, adapted to reduce a residual activation of the innate immune response in the viral vector 2, removing its residual toxicity and enabling its related administration without impairing the hepatic transduction efficiency of the viral vector;
development and use of the murine chimeric protein 10.

Advantageously, the viral vector 2 is depleted of viral coding sequences, preventing the viral vector 2 from producing proteins necessary for its own replication.

In such case, to enable a muscle-specific expression of the murine chimeric protein 1, a second expression cassette has been designed, such as a minimum transcriptional unit, conveyed by the viral vector 2 enabling its intra-muscular administration 3, comprising:

the muscular promoter;

at least one positive regulating element; and portions of a gene of interest transcribed by the RNA polymerases during the transcription process; and a starting site of the transcription process;

a DNA sequence cloned through restriction enzymes, such as, for example, ClaI and SacI, and adapted to code for the murine chimeric protein 10, such as, for example, a chimeric protein mLDLR/mTf; and a post-transcriptional regulatory element of the Woodchuck hepatitis WPRE virus, designed for increasing the amount of not implanted, nuclear and cytoplasmic RNA, positively affecting the amount of developed murine chimeric protein 10.

In particular, the murine chimeric protein 10, through the genic transfer technology according to the present invention, expressed through the adenoviral vector of the helper-dependent type under the control of the muscular promoter, is a fusion protein among the low-density lipoproteins (LDL) and a plurality of glycoproteins, such as, for example, transferrin, being equipped on its N-terminal side with a murine receptor (LDLR) adapted to bind the low-density lipoproteins (LDL) and on its C-terminal side with two or more murine glycoproteins adapted to be connected with the receptors of the murine glycoproteins internalized through endocytosis in the liver or in other tissues, such as, for example, TfR1 and TfR2.

Figure 10:
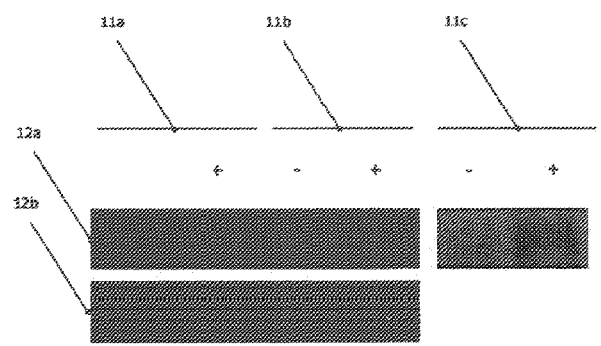

As shown in FIG. 10, a verification test has been performed on the functionality of a plasmid precursor by transfecting murine muscular cells (C2C12), treated with different growing means 11a, 11b, 11c, depending on an antigen 12a, such as, for example, αLDLR or other similar one, and on a control antigen 12b, such as, for example, αGAPDH or other similar one.

Figure 11:
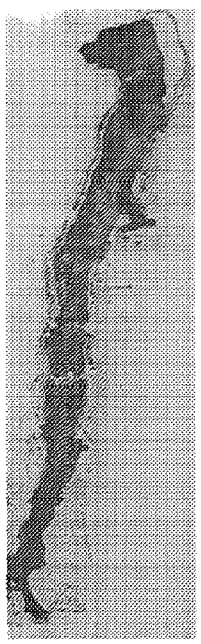
Figure 12:
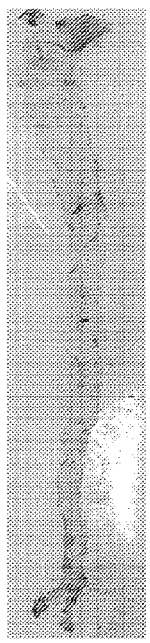
Figure 13:
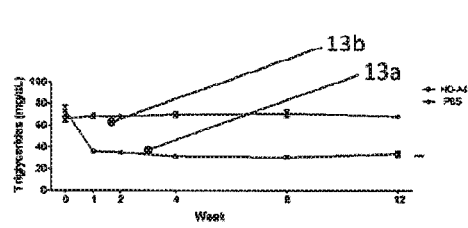
Figure 14:
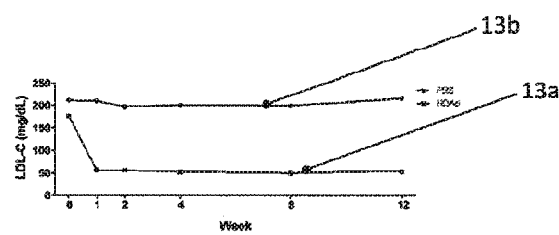
Figure 15:
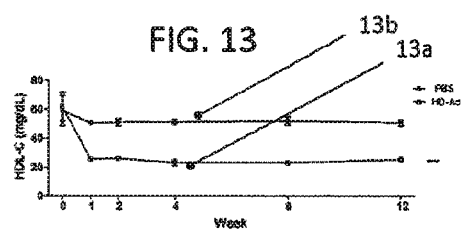
Figure 16:
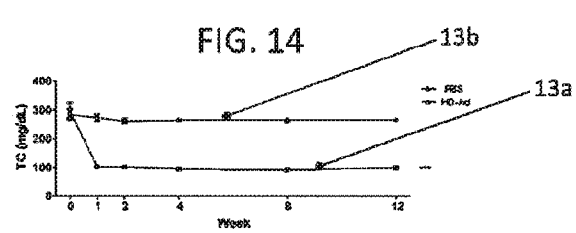
Figure 17:
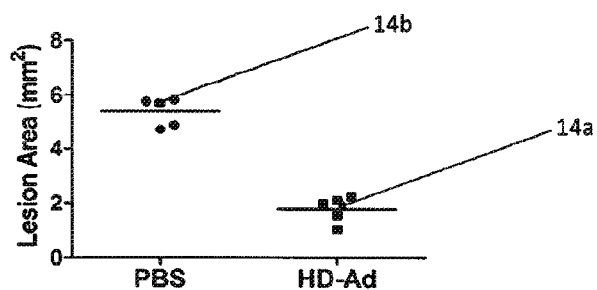

Finally, FIGS. 11-17 show, as an example, an embodiment of the genic transfer technology according to the present invention, in a murine model of family hypercholesterolaemia, through the following operating steps:—providing a first sample of cavies, such as, for example, mice, rats or other similar ones, deficient of the LDL receptor and treated with the viral vector HD-AdMCK-mLDLRmTfR expressing the murine chimeric protein mLDLR/mTf, and providing a second sample of cavies treated with a physiologic solution, adapted to operate as control sample; withdrawing a plurality of samples of aorta, as shown in FIG. 11, from the first sample of cavies during a time interval preferably covering 12 weeks;—determining with serum 13a the total cholesterol, HDL, LDL, triglycerides, etc., present in the sample taken from the first sample of cavies, as shown in FIGS. 13-16;—measuring an area of atherosclerotic lesion 14a induced on the first sample of cavies, as shown in FIG. 17;—withdrawing a plurality of samples of aorta, as shown in FIG. 12, from the second sample of cavies during a time interval preferably covering 12 weeks;—determining with serum 13b the total cholesterol, HDL, LDL, triglycerides, etc., present in the sample taken from the second sample of cavies, as shown in FIGS. 13-16; and—measuring an area of atherosclerotic lesion 14b induced on the second sample of cavies, as shown in FIG. 17. Consequently, as shown in FIGS. 13-17, the injection of the murine chimeric protein mLDLR/mTfR through administration of the adenoviral vector of the helper-dependent type, has determined the regression of the atherosclerotic lesion, and a lowering of total cholesterol, HDL, LDL, triglycerides in the first sample of cavies.

The invention claimed is:

1. A viral vector encoding a chimeric protein comprising a first cDNA sequence of SEQ ID: 2 encoding a portion of a human low-density lipoprotein receptor fused to a second cDNA sequence of SEQ ID: 3 encoding a human transferrin.

2. The viral vector of claim 1 wherein the sequence encoding the chimeric protein is contained in an expression cassette comprising, a muscle specific promoter of SEQ ID: 1 and post transcriptional regulatory elements encoded by SEQ ID: 4; such that the cassette enables muscle specific expression of the chimeric protein.

3. A chimeric protein encoded by the viral vector of claim 1.

4. A method of treating a human, comprising administering the viral vector of claim 1 via intramuscular administration.

5. A method of treating a human, comprising administering the viral vector of claim 2 via intramuscular administration.

6. A method of treating dislipidemia in a human, comprising administering the viral vector of claim 1 or 2 via intramuscular administration.

7. The method of claim 6 wherein the dislipidemia is familial hypercholesterolaemia.

* * * * *

SEQUENCE LISTING

```
<160> NUMBER OF SEQ ID NOS: 5

<210> SEQ ID NO 1
<211> LENGTH: 6632
<212> TYPE: DNA
<213> ORGANISM: ARTIFICIAL SEQUENCE
<220> FEATURE:
<223> OTHER INFORMATION: SEQUENCE IS SYNTHESIZED

<400> SEQUENCE: 1
tcgagggcgc gccgcggccg ctctttgtaa tgaaaaaaaa aaaaaaaagg tcagggccag      60
gcatggtgac tggggccttt aattccagca ttccaggagg cagagccaag aggatctctg     120
tgagttcaag gccatcctgg tctatagaga gagttccaga acagccaggg ctacagataa     180
acccatctgg aaaaacaaag ttgaatgacc caagaggggt tctcagaggg tggcgtgtgc     240
tccctggcaa gccatatgaca tggccggggc ctgcctctct ctgcctctga ccctcagtgg     300
ctcccatgaa ctccttgccc aatggcatct tttcctgcg ctccttgggt tattccagtc      360 tccctcagc attccttcct cagggcctcg ctcttctctc tgctccctcc ttgcacagct      420
ggctctgtcc acctcagatg tcacagtgct ctctcagagg aggaaggcac catgtaccct     480
ctgtttccca ggtaagggtt caatttttaa aaatggtttt ttgtttgttt gtttgtttgt     540
ttgtttgttt gtttttcaag acagggctcc tctgtgtagt cctaactgtc ttgaaactcc     600
```

-continued

```
ctctgtagac caggtcgacc tcgaactctt gaaacctgcc acggaccacc cagtcaggta      660
tggaggtccc tggaatgagc gtcctcgaag ctaggtgggt aagggttcgg cggtgacaaa      720
cagaaacaaa cacagaggca gtttgaatct gagtgtattt tgcagctctc aagcagggga      780
ttttatacat aaaaaaaaaa aaaaaaaaaa aaccaaacat tacatctctt agaaactata      840
tccaatgaaa caatcacaga taccaaccaa aaccattggg cagagtaaag cacaaaaatc      900
atccaagcat tacaactctg aaaccatgta ttcagtgaat cacaaacaga acaggtaaca      960
tcattattaa tataaatcac caaatataaa caattctaaa aggatgtatc cagtgggggc     1020
tgtcgtccaa ggctagtggc agatttccag gagcaggtta gtaaatctta accactgaac     1080
taactctcca gccccatggt caattattat ttagcatcta gtgcctaatt ttttttttata    1140 aatcttcact atgtaattta aaactatttt aattcttcct aattaaggct ttctttacca     1200
tataccaaaa ttcacctcca atgacacacg cgtagccata tgaaatttta ttgttgggaa     1260
aatttgtacc tatcataata gttttgtaaa tgatttaaaa agcaaagtgt tagccgggcg     1320
tggtggcaca cgcctttaat ccctgcactc gggaggcagg ggcaggagga tttctgagtt     1380
tgaggccagc ctggtctaca gagtgagttc caggacagcc agggctacac agagaaaccc     1440
tgtctcgaac ccccccacccc ccaaaaaaag caaagtgttg gtttccttgg ggataaagtc    1500
atgttagtgg cccatctcta ggcccatctc acccattatt ctcgcttaag atcttggcct     1560
aggctaccag gaacatgtaa ataagaaaag gaataagaga aaacaaaaca gagagattgc     1620
catgagaact acggctcaat attttttctc tccggcgaag agttccacaa ccatctccag     1680
gaggcctcca cgttttgagg tcaatggcct cagtctgtgg aacttgtcac acagatctta     1740
ctggaggtgg tgtggcagaa acccattcct tttagtgtct tgggctaaaa gtaaaaggcc     1800
cagaggaggc ctttgctcat ctgaccatgc tgacaaggaa cacgggtgcc aggacagagg     1860
ctggacccca ggaacacctt aaacacttct tcccttctcc gcccctaga gcaggctccc      1920 ctcaccagcc tgggcagaaa tgggggaaga tggagtgaag ccatactggc tactccagaa     1980
tcaacagagg gagccggggg caatactgga gaagctggtc tccccccagg ggcaatcctg    2040
gcacctccca ggcagaagag gaaacttcca cagtgcatct cacttccatg aatcccctcc    2100
tcggactctg aggtccttgg tcacagctga ggtgcaaaag gctcctgtca tattgtgtcc    2160
tgctctggtc tgccttcaca gcttgggggc cactagccc acctctccct agggatgaga     2220
gcagccacta tgggtctagg ctgcccatgt aaggaggcaa ggcctgggga cacccgagat    2280
gcctggttat aattaaccca gacatgtggc tgctccccc ccccaacacc tgctgcctga     2340
gcctcacccc caccccggtg cctgggtctt aggctctgta caccatggag gagaagctcg    2400
ctctaaaaat aaccctgtcc ctggtggatc cagggtggag gggcaggctg agggcggcca    2460
cttccctcag ccgcagtttg ttttcccaag aatggttttt ctgcttctgt agcttttcct     2520
gtcaattctg ccatggtgga gcagcctgca ctgggcttct gggagaaacc aaaccgggtt    2580
ctaacctttc agctacagtc attgcctttc ctgtagatgg gcgactacag ccccaccccc    2640 accccgtct cctgtatcct tcctgggcct ggggatccta ggctttcact ggaaatttcc     2700
ccccaggtgc tgtaggctag agtcacggct cccaagaaca gtgcttgcct ggcatgcatg    2760
gttctgaacc tccaactgca aaaatgaca catacccttga cccttggaag gctgaggcag    2820
ggggattgcc atgagtgcaa agccagactg ggtggcatag ttagaccctg tctcaaaaaa    2880
ccaaaaacaa ttaaataact aaagtcaggc aagtaatcct actcaggaga ctgaggcaga    2940
gggattgtta catgtctgag gccagcctgg actacatagg gtttcaggct agccctgtct    3000
```

```
acagagtaag gccctatttc aaaaacacaa acaaaatggt tctcccagct gctaatgctc    3060
accaggcaat gaagcctggt gagcattagc aatgaaggca atgaaggagg gtgctggcta    3120
catcaggctg tgggggactg agggcaggct gtaacaggct tgggggccag ggcttatacg    3180
tgcctgggac tcccaaagta ttactgttcc atgttcccgg cgaagggcca gctgtccccc    3240
gccagctaga ctcagcactt agtttaggaa ccagtgagca agtcagccct ggggcagcc     3300 catacaaggc catggggctg gcaagctgc acgcctgggt ccggggtggg cacggtgccc     3360
gggcaacgag ctgaaagctc atctgctctc aggggcccct ccctgggac agcccctcct    3420 ggctagtcac accctgtagg ctcctctata taacccaggg gcacagggc tgccccggg     3480 tcaccaccac ctccacagca cagacagaca ctcaggagcc agccagccag gtagggactg    3540
agagaaatca ctggggtggg agtggggcgt gggagtccaa gggtctgctc acccagtcat    3600
gttatggttg tggattttgc agcacaagtt gtggggacaa atgtctggga cacctaggtc    3660
tcaatagcca ccaagtgtcc cctccttgca aggcagggtg ggctggaact tagtttagca    3720
gagttaatgg cccacacaaa gacagttgtc tcagtgacac ctgtcagtgg cccttaaact    3780
ttgtaaccat gtggacctgt gttgcagctc tgtgaccttg tgtctcactg tcctggtctg    3840
tctctatgtc tctctgtctc tctgtctcta tctctctctt tctgtctctc tctctccctc    3900
tctctttcga gatgggtcag gggggggtgg tgttctctgc atagccctgg ctgtcctgga    3960
actcactctg tagaccagcc tggcctcgaa ctcagaaatc cacctgcctc ccaagtgctg    4020
ggattaaagg cgtgtgccac caccgcccgg cgggtctttc ttgtgtgaga cttgggggct    4080
ctcactctta caggcccctg gctttccttt gagtccttct gtctggctgt tctctgggatc    4140 ttgaaggcag gaaggactac atgactcagt ttacctggag atcttagaga atctgtgatg    4200
agtttgggga ttccgaagct ttctgcttct gcgtcttgcc tcggtgtcct gtctcctggg    4260
gtgcccctga gggaggggt agcagaggat acagaacctt ctgaagggag agatctgggc     4320
tgggagcccg gggtgtcctt gaggcccaga gcctggctgt gtgtcctcct ggccacccca    4380
gcccacctgt cccaatgctg acttagtgca aggcgagcca gcaaggaggg aggacaggtg    4440
gcagtggggg gtgaggagca tctaaaaata gccacaaagt agcagcttca agggctttgg    4500
gtctctgtct gccccacact ctttctctcag cttggtccac cttccctctc accttcctct    4560 gaggcccct tccagcccg atggaggcct gatgtccccc atggtcagtg cttcagggat     4620
ctagtcaata aaattaataa tgaaaaacaa cagtaataaa atacacgtga cgtgactggg    4680
gcagcttagg gcttagttca aatcccagtg ttcacaccct ttaaaagaca agacaaaaca    4740
aaacagctgg ctgtggggga aacatcaga atcccctgg ggaggtgggg acagggatc      4800 tgtgggctc catggccagc cagcctagct ccaggcctgc gagagaccct acctcaagat    4860
aaaaataaaa taaataaaa taaatatata aaataacaat cttgcagcac ctgaggtcac    4920
cactggaatg tgcacacctg tgcacataca tgagcctgca ctacaaacaa aatattaac    4980 agtaactgtt agaatcccag ctgcaacttc atgccaggtg ccaggtccat gctcatcagt    5040
cagggactgg aactcagaga tctcctggga aagcttcagt ctcacagatt caaaagccag    5100
agagatctag tcagagcctg ggccagag cagtgactta ggagagccgt gccttttaaa     5160
gtggaccttg tagacagcca gaggtggagg gactgggaga agtggctgaa gcctccagac    5220
tcattcccac gccacatct ggactaattt ggatcagaat ctcaggggag cccttatggc     5280
ttttctcagg tgtgcacata taatctttac cagggtcctc acacagagcc tgtcagattg    5340
```

| | |
|---|---|
| gttttcaatt tctgtgacaa acaccatgac caagacaacc tagaaaagag aaagcattaa | 5400 |
| tttgggctc agggttctgg agcggcaggg aggtgggcat ggtgctggag cagaggctgg | 5460 |
| aagctcacat ctttatcaac aaccagaggc agtgagagcc acttgggaat ggggtggctt | 5520 |
| ttcggaaatc tcaaagccca caagcaatgg cacacctcct ccaacaaggc cacacctccg | 5580 |
| aatccttccc aaacagttcc accgactggg gaccaaacat tcaaatatgt gagtctgagg | 5640 |
| ctcttctcat tcaaatcacc acagacccaa gaacaatcga ataaaatatt tgtgttatgt | 5700 |
| gccaggcact ggccgaggcg cttttcttgt cttttaatcc ctcccaagag gtcagcgatg | 5760 |
| ccacagtctc catgttacag atgagtgaac aggaaagtca acaggctcc tcagagtcac | 5820 |
| gcggctgctt gtaagttgca aagccgaaat tcgaacccag accatctgat ccagatcctt | 5880 |
| tgctgctttt attcatcttt ttatttatt ttattttatt ttaattcctg gtggcagggt | 5940 |
| ttctgtagcc caggctaccc ttgaattcac tgcaatcctc ctgcctcagt ttcagagtgt | 6000 |
| tggaattaca agcatggacc atcatgccca gttcctttgg gttgagatag agacctgtgt | 6060 |
| aggagcccag actcggctg gtctccagct ctctacgtag atgaagatga ccttgaactg | 6120 |
| ctggatttc aggcatgagc agccacaccc agatttgctg agcgccaaac tgttacccag | 6180 |
| ggtcctaagc ttgctgggca agcactctgc cagcagaacc ccagcccag atcctgtatt | 6240 |
| tttgtagttg tttttgttta tgtgactgtc cttttctggc tttagacaaa aggttttgcc | 6300 |
| ctccttttcc agctagagag actgagtccc cagcaggatc acataggcag gatgtggcca | 6360 |
| catcaggcaa cttgggctcc tgatgttttcc ttgcaaggct gaggttcaca ggggagaac | 6420 |
| cccccttttt caagcccacg gtccgacgga ctgcaagccc ccagcaactg agttcttaag | 6480 |
| tctgagcggc cgcacccggt ctgctcgcag ggtcccaaag gccgccaccc tcgactctgg | 6540 |
| ctaactagag aacccactgc ttactggctt atcgaaatta atacgactca ctatagggag | 6600 |
| acccaagctt ggtaccgagc tcggatccag cc | 6632 |

<210> SEQ ID NO 2
<211> LENGTH: 2310
<212> TYPE: DNA
<213> ORGANISM: ARTIFICIAL SEQUENCE
<220> FEATURE:
<223> OTHER INFORMATION: SEQUENCE IS SYNTHESIZED

<400> SEQUENCE: 2

| | |
|---|---|
| atggggccct ggggctggaa attgcgctgg accgtcgcct tgctcctcgc cgcggcgggg | 60 |
| actgcagtgg gcgacagatg tgaaagaaac gagttccagt gccaagacgg aaatgcatc | 120 |
| tcctacaagt gggtctgcga tggcagcgct gagtgccagg atggctctga tgagtcccag | 180 |
| gagacgtgct gtctgtcac ctgcaaatcc ggggacttca gctgtggggg ccgtgtcaac | 240 |
| cgctgcattc ctcagttctg gaggtgcgat ggccaagtgg actgcgacaa cggctcagac | 300 |
| gagcaaggct gtccccccaa gacgtgctcc caggacgagt ttcgctgcca cgatgggaag | 360 |
| tgcatctctc ggcagttcgt ctgtgactca gaccgggact gcttggacgg ctcagacgag | 420 |
| gcctcctgcc cggtgctcac ctgtggtccc gccagcttcc agtgcaacag ctccacctgc | 480 |
| atccccagc tgtgggcctg cgacaacgac cccgactgcg aagatggctc ggatgagtgg | 540 |
| ccgcagcgct gtagggggtct ttacgtgttc caaggggaca gtagcccctg ctcggccttc | 600 |
| gagttccact gcctaagtgg cgagtgcatc cactccagct ggcgctgtga tggtggcccc | 660 |
| gactgcaagg acaaatctga cgaggaaaac tgcgctgtgg ccacctgtcg ccctgacgaa | 720 |
| ttccagtgct ctgatggaaa ctgcatccat ggcagccggc agtgtgaccg ggaatatgac | 780 |

```
tgcaaggaca tgagcgatga agttggctgc gttaatgtga cactctgcga gggacccaac    840
aagttcaagt gtcacagcgg cgaatgcatc accctggaca aagtctgcaa catggctaga    900
gactgccggg actggtcaga tgaacccatc aaagagtgcg ggaccaacga atgcttggac    960
aacaacggcg gctgttccca cgtctgcaat gaccttaaga tcggctacga gtgcctgtgc   1020
cccgacggct tccagctggt ggcccagcga agatgcgaag atatcgatga gtgtcaggat   1080
cccgacacct gcagccagct ctgcgtgaac ctggagggtg gctacaagtg ccagtgtgag   1140
gaaggcttcc agctggaccc ccacacgaag gcctgcaagg ctgtgggctc catcgcctac   1200
ctcttcttca ccaaccggca cgaggtcagg aagatgacgc tggaccggag cgagtacacc   1260
agcctcatcc ccaacctgag gaacgtggtc gctctggaca cggaggtggc cagcaataga   1320
atctactggt ctgacctgtc ccagagaatg atctgcagca cccagcttga cagagcccac   1380
ggcgtctctt cctatgacac cgtcatcagc agggacatcc aggcccccga cgggctggct   1440
gtggactgga tccacagcaa catctactgg accgactctg tcctgggcac tgtctctgtt   1500
gcggatacca agggcgtgaa gaggaaaacg ttattcaggg agaacggctc caagccaagg   1560
gccatcgtgg tggatcctgt tcatggcttc atgtactgga ctgactgggg aactcccgcc   1620
aagatcaaga aggggggcct gaatggtgtg gacatctact cgctggtgac tgaaaacatt   1680
cagtggccca atggcatcac cctagatctc ctcagtggcc gcctctactg ggttgactcc   1740
aaacttcact ccatctcaag catcgatgtc aatgggggca accggaagac catcttggag   1800
gatgaaaaga ggctggccca ccccttctcc ttggccgtct ttgaggacaa agtattttgg   1860
acagatatca tcaacgaagc catttttcagt gccaaccgcc tcacaggttc cgatgtcaac   1920
ttgttggctg aaaacctact gtccccagag gatatggtcc tcttccacaa cctcacccag   1980
ccaagaggag tgaactggtg tgagaggacc accctgagca atggcggctg ccagtatctg   2040
tgcctccctg ccccgcagat caaccccac tcgcccaagt ttacctgcgc ctgcccggac   2100
ggcatgctgc tggccaggga catgaggagc tgcctcacag aggctgaggc tgcagtggcc   2160
acccaggaga catccaccgt caggctaaag gtcagctcca cagccgtaag gacacagcac   2220
acaaccaccc ggcctgttcc cgacacctcc cggctgcctg ggccacccc tgggctcacc   2280 acggtggaga tagtgacaat gtctcaccaa                                    2310
```

<210> SEQ ID NO 3
<211> LENGTH: 2097
<212> TYPE: DNA
<213> ORGANISM: ARTIFICIAL SEQUENCE
<220> FEATURE:
<223> OTHER INFORMATION: SEQUENCE IS SYNTHESIZED

<400> SEQUENCE: 3

```
atgaggctcg ccgtgggagc cctgctggtc tgcgccgtcc tggggctgtg tctggctgtc     60
cctgataaaa ctgtgagatg gtgtgcagtg tcggagcatg aggccactaa gtgccagagt    120
ttccgcgacc atatgaaaag cgtcattcca tccgatggtc ccagtgttgc ttgtgtgaag    180
aaagcctcct accttgattg catcagggcc attgcggcaa acgaagcgga tgctgtgaca    240
ctggatgcag gtttggtgta tgatgcttac ctggctccca ataacctgaa gcctgtggtg    300
gcagagttct atgggtcaaa agaggatcca cagactttct attatgctgt tgctgtggtg    360
aagaaggata gtgccttcca gatgaaccag cttcgaggca agaagtcctg ccacacgggt    420
ctaggcaggt ccgctgggtg gaacatcccc ataggcttac tttactgtga cttacctgag    480
```

| | |
|---|---|
| ccacgtaaac ctcttgagaa agcagtggcc aatttcttct cgggcagctg tgccccttgt | 540 |
| gcggatggga cggacttccc ccagctgtgt caactgtgtc cagggtgtgg ctgctccacc | 600 |
| cttaaccaat acttcggcta ctcgggagcc ttcaagtgtc tgaaggatgg tgctggggat | 660 |
| gtggcctttg tcaagcactc gactatattt gagaacttgg caaacaaggc tgacagggac | 720 |
| cagtatgagc tgctttgcct ggacaacacc cggaagccgg tagatgaata caaggactgc | 780 |
| cacttggccc aggtcccttc tcataccgtc gtggcccgaa gtatgggcgg caaggaggac | 840 |
| ttgatctggg agcttctcaa ccaggcccag gaacattttg gcaaagacaa atcaaaagaa | 900 |
| ttccaactat tcagctctcc tcatgggaag gacctgctgt ttaaggactc tgcccacggg | 960 |
| tttttaaaag tccccccag gatggatgcc aagatgtacc tgggctatga gtatgtcact | 1020 |
| gccatccgga atctacggga aggcacatgc ccagaagccc aacagatga atgcaagcct | 1080 |
| gtgaagtggt gtgcgctgag ccaccacgag aggctcaagt gtgatgagtg gagtgttaac | 1140 |
| agtgtaggga aaatagagtg tgtatcagca gagaccaccg aagactgcat cgccaagatc | 1200 |
| atgaatggag aagctgatgc catgagcttg gatggagggt ttgtctacat agcgggcaag | 1260 |
| tgtggtctgg tgcctgtctt ggcagaaaac tacaataaga gcgataattg tgaggataca | 1320 |
| ccagaggcag ggtattttgc tatagcagtg gtgaagaaat cagcttctga cctcacctgg | 1380 |
| gacaatctga aaggcaagaa gtcctgccat acggcagttg gcagaaccgc tggctggaac | 1440 |
| atccccatgg gcctgctcta caataagatc aaccactgca gatttgatga attttttcagt | 1500 |
| gaaggttgtg ccctggggtc taagaaagac tccagtctct gtaagctgtg tatgggctca | 1560 |
| ggcctaaacc tgtgtgaacc caacaacaaa gagggatact acggctacac aggcgctttc | 1620 |
| aggtgtctgg ttgagaaggg agatgtggcc tttgtgaaac accagactgt cccacagaac | 1680 |
| actgggggaa aaaaccctga tccatgggct aagaatctga atgaaaaaga ctatgagttg | 1740 |
| ctgtgccttg atggtaccag gaaacctgtg gaggagtatg cgaactgcca cctggccaga | 1800 |
| gccccgaatc acgctgtggt cacacggaaa gataaggaag cttgcgtcca caagatatta | 1860 |
| cgtcaacagc agcacctatt tggaagcaac gtaactgact gctcgggcaa cttttgtttg | 1920 |
| ttccggtcgg aaaccaagga ccttctgttc agagatgaca cagtatgttt ggccaaactt | 1980 |
| catgacagaa acacatatga aaaatactta ggagaagaat atgtcaaggc tgttggtaac | 2040 |
| ctgagaaaat gctccacctc atcactcctg gaagcctgca ctttccgtag accttaa | 2097 |

```
<210> SEQ ID NO 4
<211> LENGTH: 847
<212> TYPE: DNA
<213> ORGANISM: ARTIFICIAL SEQUENCE
<220> FEATURE:
<223> OTHER INFORMATION: SEQUENCE IS SYNTHESIZED

<400> SEQUENCE: 4
```

| | |
|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg gctcggctg | 360 |
| ttgggcactg acaattccgt ggtgttgtcg gggaagctga cgtcctttcc atggctgctc | 420 |
| gcctgtgttg ccacctggat tctgcgcggg acgtccttct gctacgtccc ttcggccctc | 480 |

```
aatccagcgg accttccttc ccgcggcctg ctgccggctc tgcggcctct tccgcgtctt    540
cgccttcgcc ctcagacgag tcggatcctc ctttgggccg cctccccgcc tgtttcgcct    600
cggcgtccgg tccgtgttgc ttggtcttca cctgtgcaga cttgcgaacc atggattcca    660
ccgtgaactt tgtctcctgg catgcaaatc gtcaacttgg catgccaagt gaaaaaaatg    720
ctttatttgt gaaatttgtg atgctattgc tttatttgta accattataa gctgcaataa    780
acaagttaac aacaacaatt gcattcattt tatgtttcag gttcagggca tatggagctg    840
gcgcgcc                                                              847

<210> SEQ ID NO 5
<211> LENGTH: 1468
<212> TYPE: PRT
<213> ORGANISM: ARTIFICIAL SEQUENCE
<220> FEATURE:
<223> OTHER INFORMATION: SEQUENCE IS SYNTHESIZED

<400> SEQUENCE: 5

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285
```

```
Cys Ile Thr Leu Asp Lys Val Cys Asn Met Ala Arg Asp Cys Arg Asp
290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
                340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
                420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
                500                 505                 510

Arg Glu Asn Gly Ser Lys Pro Arg Ala Ile Val Val Asp Pro Val His
            515                 520                 525

Gly Phe Met Tyr Trp Thr Asp Trp Gly Thr Pro Ala Lys Ile Lys Lys
530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
            595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
                675                 680                 685

Pro His Ser Pro Lys Phe Thr Cys Ala Cys Pro Asp Gly Met Leu Leu
        690                 695                 700

Ala Arg Asp Met Arg Ser Cys Leu Thr Glu Ala Glu Ala Ala Val Ala
```

-continued

```
            705                 710                 715                 720
        Thr Gln Glu Thr Ser Thr Val Arg Leu Lys Val Ser Ser Thr Ala Val
                        725                 730                 735

Arg Thr Gln His Thr Thr Thr Arg Pro Val Pro Asp Thr Ser Arg Leu
                        740                 745                 750

Pro Gly Ala Thr Pro Gly Leu Thr Val Glu Ile Val Thr Met Ser
                        755                 760                 765

His Gln Met Arg Leu Ala Val Gly Ala Leu Leu Val Cys Ala Val Leu
                        770                 775                 780

Gly Leu Cys Leu Ala Val Pro Asp Lys Thr Val Arg Trp Cys Ala Val
        785                 790                 795                 800

Ser Glu His Glu Ala Thr Lys Cys Gln Ser Phe Arg Asp His Met Lys
                        805                 810                 815

Ser Val Ile Pro Ser Asp Gly Pro Ser Val Ala Cys Val Lys Lys Ala
                        820                 825                 830

Ser Tyr Leu Asp Cys Ile Arg Ala Ile Ala Ala Asn Glu Ala Asp Ala
                        835                 840                 845

Val Thr Leu Asp Ala Gly Leu Val Tyr Asp Ala Tyr Leu Ala Pro Asn
        850                 855                 860

Asn Leu Lys Pro Val Val Ala Glu Phe Tyr Gly Ser Lys Glu Asp Pro
        865                 870                 875                 880

Gln Thr Phe Tyr Tyr Ala Val Ala Val Val Lys Lys Asp Ser Gly Phe
                        885                 890                 895

Gln Met Asn Gln Leu Arg Gly Lys Lys Ser Cys His Thr Gly Leu Gly
                        900                 905                 910

Arg Ser Ala Gly Trp Asn Ile Pro Ile Gly Leu Leu Tyr Cys Asp Leu
                        915                 920                 925

Pro Glu Pro Arg Lys Pro Leu Glu Lys Ala Val Ala Asn Phe Phe Ser
                        930                 935                 940

Gly Ser Cys Ala Pro Cys Ala Asp Gly Thr Asp Phe Pro Gln Leu Cys
        945                 950                 955                 960

Gln Leu Cys Pro Gly Cys Gly Cys Ser Thr Leu Asn Gln Tyr Phe Gly
                        965                 970                 975

Tyr Ser Gly Ala Phe Lys Cys Leu Lys Asp Gly Ala Gly Asp Val Ala
                        980                 985                 990

Phe Val Lys His Ser Thr Ile Phe Glu Asn Leu Ala Asn Lys Ala Asp
                        995                 1000                1005

Arg Asp Gln Tyr Glu Leu Leu Cys Leu Asp Asn Thr Arg Lys Pro Val
                        1010                1015                1020

Asp Glu Tyr Lys Asp Cys His Leu Ala Gln Val Pro Ser His Thr Val
        1025                1030                1035                1040

Val Ala Arg Ser Met Gly Gly Lys Glu Asp Leu Ile Trp Glu Leu Leu
                        1045                1050                1055

Asn Gln Ala Gln Glu His Phe Gly Lys Asp Lys Ser Lys Glu Phe Gln
                        1060                1065                1070

Leu Phe Ser Ser Pro His Gly Lys Asp Leu Leu Phe Lys Asp Ser Ala
                        1075                1080                1085

His Gly Phe Leu Lys Val Pro Pro Arg Met Asp Ala Lys Met Tyr Leu
                        1090                1095                1100

Gly Tyr Glu Tyr Val Thr Ala Ile Arg Asn Leu Arg Glu Gly Thr Cys
        1105                1110                1115                1120

Pro Glu Ala Pro Thr Asp Glu Cys Lys Pro Val Lys Trp Cys Ala Leu
                        1125                1130                1135
```

-continued

Ser His His Glu Arg Leu Lys Cys Asp Glu Trp Ser Val Asn Ser Val
            1140                1145                1150

Gly Lys Ile Glu Cys Val Ser Ala Glu Thr Thr Glu Asp Cys Ile Ala
        1155                1160                1165

Lys Ile Met Asn Gly Glu Ala Asp Ala Met Ser Leu Asp Gly Gly Phe
    1170                1175                1180

Val Tyr Ile Ala Gly Lys Cys Gly Leu Val Pro Val Leu Ala Glu Asn
1185                1190                1195                1200

Tyr Asn Lys Ser Asp Asn Cys Glu Asp Thr Pro Glu Ala Gly Tyr Phe
            1205                1210                1215

Ala Ile Ala Val Val Lys Lys Ser Ala Ser Asp Leu Thr Trp Asp Asn
        1220                1225                1230

Leu Lys Gly Lys Lys Ser Cys His Thr Ala Val Gly Arg Thr Ala Gly
            1235                1240                1245

Trp Asn Ile Pro Met Gly Leu Leu Tyr Asn Lys Ile Asn His Cys Arg
    1250                1255                1260

Phe Asp Glu Phe Phe Ser Glu Gly Cys Ala Pro Gly Ser Lys Lys Asp
1265                1270                1275                1280

Ser Ser Leu Cys Lys Leu Cys Met Gly Ser Gly Leu Asn Leu Cys Glu
            1285                1290                1295

Pro Asn Asn Lys Glu Gly Tyr Tyr Gly Tyr Thr Gly Ala Phe Arg Cys
        1300                1305                1310

Leu Val Glu Lys Gly Asp Val Ala Phe Val Lys His Gln Thr Val Pro
    1315                1320                1325

Gln Asn Thr Gly Gly Lys Asn Pro Asp Pro Trp Ala Lys Asn Leu Asn
        1330                1335                1340

Glu Lys Asp Tyr Glu Leu Leu Cys Leu Asp Gly Thr Arg Lys Pro Val
1345                1350                1355                1360

Glu Glu Tyr Ala Asn Cys His Leu Ala Arg Ala Pro Asn His Ala Val
            1365                1370                1375

Val Thr Arg Lys Asp Lys Glu Ala Cys Val His Lys Ile Leu Arg Gln
        1380                1385                1390

Gln Gln His Leu Phe Gly Ser Asn Val Thr Asp Cys Ser Gly Asn Phe
    1395                1400                1405

Cys Leu Phe Arg Ser Glu Thr Lys Asp Leu Leu Phe Arg Asp Asp Thr
    1410                1415                1420

Val Cys Leu Ala Lys Leu His Asp Arg Asn Thr Tyr Glu Lys Tyr Leu
1425                1430                1435                1440

Gly Glu Glu Tyr Val Lys Ala Val Gly Asn Leu Arg Lys Cys Ser Thr
            1445                1450                1455

Ser Ser Leu Leu Glu Ala Cys Thr Phe Arg Arg Pro
        1460                1465